United States Patent [19]

Gaertner

[11] 4,211,547

[45] Jul. 8, 1980

[54] N-PHOSPHONOME-THYLIMINODIACETONITRILE AND CERTAIN DERIVATIVES THEREOF

[75] Inventor: Van R. Gaertner, Ballwin, Mo.

[73] Assignee: Monsanto Company, St. Louis, Mo.

[21] Appl. No.: 972,547

[22] Filed: Dec. 22, 1978

[51] Int. Cl.$^2$ .................. C07C 121/43; A01N 9/36
[52] U.S. Cl. .................................. 71/86; 260/940; 260/465 E; 260/942; 260/465.5 R; 260/558 A; 260/561 A
[58] Field of Search .......... 260/465.5 R, 465 E, 260/940; 71/86

[56] References Cited

U.S. PATENT DOCUMENTS

| | | | |
|---|---|---|---|
| 3,455,675 | 7/1969 | Irani | 71/86 |
| 3,754,035 | 8/1973 | Grayson | 260/465.5 R X |
| 3,923,877 | 12/1975 | Barton | 260/502.5 |
| 4,008,296 | 2/1977 | Barton | 260/940 |
| 4,067,719 | 1/1978 | Dutra | 71/86 |
| 4,083,898 | 4/1978 | Dutra | 260/970 |
| 4,089,671 | 5/1978 | Dutra | 71/86 |
| 4,120,689 | 10/1979 | Dutra | 71/86 |

FOREIGN PATENT DOCUMENTS

| | | | |
|---|---|---|---|
| 50-84532 | 8/1975 | Japan | 71/86 |
| 52-144656 | 12/1977 | Japan | 71/86 |

*Primary Examiner*—Joseph Paul Brust
*Attorney, Agent, or Firm*—Arnold H. Cole; Donald W. Peterson

[57] ABSTRACT

N-phosphonomethyliminodiacetonitrile and certain derivatives thereof are novel compounds which can be used as herbicides themselves and/or can be converted to known herbicides.

9 Claims, No Drawings

N-PHOSPHONOMETHYLIMINODIACETONITRILE AND CERTAIN DERIVATIVES THEREOF

This invention relates to a class of novel organic chemical compounds. More particularly, this invention is concerned with N-phosphonomethyliminodiacetonitrile, aryl esters and salts thereof, and the corresponding diacetamide. The compounds prepared herein have been found to possess useful herbicidal activity and/or they can be converted to known herbicidally active materials.

U.S. Pat. Nos. 3,923,877 and 4,008,296 describe the reaction of a dihydrocarbylphosphite with 1,3,5-tricyanomethylhexahydro-1,3,5-triazine in the presence of an acidic catalyst to produce a diester of N-phosphonomethylglycinonitrile. This product is then hydrolyzed to N-phosphonomethylglycine, a known herbicide. U.S. Pat. Nos. 4,067,719 and 4,083,898 describe the preparation of diaryl esters of N-phosphonomethylglycinonitrile using a corresponding phosphite diester and the same triazine without the need for a catalyst. Hydrolysis of the diesters to monoesters is also described, as well as the hydrolysis of such esters to N-phosphonomethylglycine. U.S. Pat. No. 3,455,675 teaches the preparation of N-phosphonomethyliminodiacetic acid and its use as a herbicide.

The novel compounds of the present invention can be illustrated by the formula

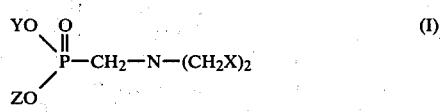

wherein X represents cyano or carbamoyl, and Y represents hydrogen, phenyl, tolyl or halogenated phenyl and halogenated tolyl, and Z represents Y or an agriculturally acceptable cation. The agriculturally acceptable cations are those which are commonly used in herbicidal formulations to form the salt of a free acid including, but not limited to, metals of Groups I and II having an atomic number no greater than 30, ammonium, and aliphatic ammonium cations. It will be understood that where the cation is a divalent metal, the resultant salt is formed with two molecules of the free acid, and can be represented as either

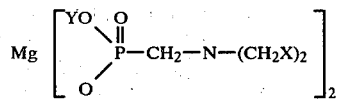

or $Z = \frac{1}{2}$ Mg.

The aryl esters of formula (I) are smoothly prepared by the reaction of iminodiacetonitrile, formaldehyde and a triaryl phosphite. The reaction should be conducted at an elevated temperature, preferably in the range of 80°–120° C., and, in general, substantially equimolar quantities of each reactant are employed.

The free acid dinitrile of formula (I), where Y and Z are hydrogen, is prepared by first forming an alkali metal salt of aminomethylphosphonic acid, reacting the salt with formaldehyde, and thereafter treating the intermediate product with potassium cyanide. Room temperature or below (0°–25° C.) is maintained during both steps. At least 2 moles of each of formaldehyde and potassium cyanide are employed per mole of aminomethylphosphonic acid, and an excess of the former two reactants can be used. The pH during the reaction should be kept in the range of 8–10, and periodic additions of hydrochloric acid or the like can be used to make the needed adjustments. The free acid diacetamide is prepared in the same manner except that the product after cyanide addition is heated at about 40°–50° C. High pressure liquid chromatography ion exchange is conveniently used to isolate the desired product. The salts of formula (I), where Z is an agriculturally acceptable cation, are obtained by simple neutralization using well known techniques.

The examples which follow will serve to further illustrate the preparation of specific individual compounds of the class described.

EXAMPLE 1

A mixture of 9.5 grams (0.1 mole) of iminodiacetonitrile, 3.0 grams of para-formaldehyde, and 31 grams of triphenyl phosphite was stirred and heated in an oil bath to 85°–90° C. for 2 hours. The dark viscous oil obtained is stirred with 100 ml. of water, and 100 ml. of ether is added with further stirring. A finely divided solid which precipitates is removed by filtration and rinsed with ether. The solid is then dissolved in chloroform, dried with magnesium sulfate, and filtered to give a colorless solution. The chloroform was removed by rotoevaporation, and the warm residue was treated with ether to form crystals which are separated by filtration and rinsed. The white crystals obtained were 21.2 grams of N-(diphenylphosphonomethyl)iminodiacetonitrile, m.p. 87°–88° C. Elemental analysis gave 59.77% carbon, 5.05% hydrogen, 12.32% nitrogen and 9.07% phosphorus as against calculated values of 59.82%, 4.73%, 12.31% and 9.08% respectively for $C_{17}H_{16}N_3O_3P$.

EXAMPLE 2

A mixture of 4.8 grams of iminodiacetonitrile, 1.5 grams of para-formaldehyde and 17.6 grams of tri(o-tolyl)phosphite was prepared and treated as described in Example 1. The rotoevaporation gave 23 grams of a viscous amber oil, of which 10 grams was subjected to high pressure liquid chromatography on silica gel in ethyl acetate/cyclohexane (60:40). The product, 7.6 grams, was again chromatographed in a 40:60 mixture, and there was obtained from fractions 30–48, 6.7 grams of N-[di(o-tolyl)phosphonomethyl]iminoacetonitrile as a colorless viscous oil, $n_D^{26} = 1.5410$. Elemental analysis gave 61.72% carbon, 5.64% hydrogen, 11.55% nitrogen and 8.39% phosphorus as against calculated values of 61.78%, 5.46%, 11.38% and 8.39% respectively for $C_{19}H_{20}N_3O_3P$.

EXAMPLE 3

A mixture of 4.8 grams of iminodiacetonitrile, 1.5 grams of para-formaldehyde and 25.7 grams of tri(m-trifluoromethylphenyl) phosphite was prepared and treated as described in Example 1. The rotoevaporation gave a viscous amber oil which was divided into two portions, each of which was subjected to high pressure liquid chromatography on silica gel in ethyl acetate/cyclohexane (40:60). Fractions 35–53 from each portion were combined and rechromatographed in ethyl acetate/cyclohexane (30:70). The product obtained from fractions 46–64 was 2.92 grams of N-[di(m-trifluoromethylphenyl)phosphonomethyl]iminodiacetonitrile as a colorless oil, $n_D^{23}=1.4830$. Elemental analysis gave 48.32% carbon, 3.11% hydrogen, 9.14% nitrogen and 6.91% phosphorus as against calculated values of 47.81%, 2.96%, 8.80% and 6.49% respectively for $C_{19}H_{14}F_6N_3O_3P$.

EXAMPLE 4

A mixture of 4.8 grams of iminodiacetonitrile, 1.5 grams of para-formaldehyde and 20.7 grams of tri(o-chlorophenyl) phosphite was prepared and treated as described in Example 1. The rotoevaporation gave a dark amber oil which was subjected to high pressure liquid chromatography on silica gel in ethyl acetate/cyclohexane (40:60). The product obtained from fractions 44–55 was 3.54 grams of N-[di(o-chlorophenyl)phosphonomethyl]iminodiacetonitrile as an amber oil, $n_D^{23}=1.5583$. Elemental analysis gave 49.80% carbon, 3.45% hydrogen, 10.03% nitrogen and 7.91% phosphorus as against calculated values of 49.7%, 3.44%, 10.24% and 7.55% respectively for $C_{17}H_{14}Cl_2N_3O_3P$.

EXAMPLE 5

A mixture of 4.6 grams of iminodiacetonitrile, 1.5 grams of para-formaldehyde and 23.0 grams of tri(4-chloro-m-tolyl)phosphite was prepared and treated as described in Example 1. The rotoevaporation gave a light amber oil, half of which was subjected to high pressure liquid chromatography on silica gel in ethyl acetate/cyclohexane (40:60). Fractions 22–35 gave 9.5 grams of a light yellow oil which was dried at 56° C./1 mm. The product, which crystallized on standing, was N-[di(4-chloro-m-tolyl)phosphonomethyl-]iminodiacetonitrile, m.p. 80°–83° C. Elemental analysis gave 52.64% carbon, 4.27% hydrogen, 9.12% nitrogen and 6.73% phosphorus as against calculated values of 52.07%, 4.14%, 9.59% and 7.07% respectively for $C_{19}H_{18}Cl_2N_3O_3P$.

EXAMPLE 6

A solution of 5.6 grams (0.05 mole) of aminomethylphosphonic acid in 30 ml. of water gave a pH of 1.6, and the dropwise addition of 50% sodium hydroxide raised the pH to 9. The solution was cooled to 10° C., and 8.0 grams (0.1 mole) of formalin was added dropwise, with stirring, at 10°–15° C. The pH fell to 6.1, and it was brought back to 9.0 in the same manner, followed by stirring for 30 minutes at 10°–15° C. It was then cooled to 10° C., and a solution of 6.5 grams (0.1 mole) of potassium cyanide in 30 ml. of water was added in small portions at 10°–15° C. The pH was mainly in the range of 8.5–9.5 with dilute hydrochloric acid being added to control the tendency to become more alkaline. The final pH was 9.5 which was adjusted to 9.0, and the temperature was allowed to rise to 20°–23° C. After standing overnight, the pH of the resultant yellow solution was 8.5. The solution was filtered, and the filtrate was ion exchanged on an acid resin in water by high pressure liquid chromatography, eluting with water. Fractions 14–21 gave 3.96 grams of an amber gum to which water was added. This product was chromatographed again, and fractions 25–32 gave 2.42 grams of N-phosphonomethyliminodiacetonitrile in the dihydrate form as a glassy amber gum. Elemental analysis gave 27.36% hydrogen, 4.67% hydrogen, 18.46% nitrogen and 14.34% phosphorus as against calculated values of 26.67%, 5.37%, 18.66% and 13.76% respectively for $C_5H_8N_3O_3P.2H_2O$.

EXAMPLE 7

The procedure described in Example 6 was repeated, and after the overnight standing and filtration, the resultant solution had a pH of 8.3. Half of this solution was heated to 40°–45° C. for 2 hours and then ion exchanged by high pressure liquid chromatography as described above. Fractions 6–15 gave 6.25 grams of an amber glass which was dissolved in 25 ml. of water. Crystals separated slowly, and the slurry was cooled, the solid removed by filtration, washed and dried. The product, obtained as colorless crystals, was 3.29 grams of N-phosphonomethyliminodiacetamide, m.p. 156°–158° C. (dec.), in the monohydrate form. Elemental analysis gave 24.70% carbon, 6.01% hydrogen, 16.95% nitrogen and 13.08% phosphorus as against calculated values of 24.66%, 5.79%, 17.25% and 12.72% respectively for $C_5H_{12}N_3O_5P.H_2O$.

EXAMPLE 8

A 1.20 grams portion of N-phosphonomethyliminodiacetonitrile was dissolved in 10 ml. of water at room temperature and titrated to a pH of 6.8 with small additions of magnesium hydroxide. The solution was then filtered, and the filtrate was freeze dried, with stirring, to <0.1 mm. over potassium hydroxide pellets in a dessicator. Light tan crystals formed on standing overnight and were redried for 5 hours at 56° C./0.1 mm. The product obtained was 1.2 grams of the monomagnesium salt of N-phosphonomethyliminodiacetonitrile in the tetrahydrate form. The crystals shrank up to 130° C., turned amber at 185° C., and darkened to black at 240° C. Elemental analysis gave 13.15% phosphorus as against a calculated value of 13.11% for $C_{10}H_{14}MgN_6O_6P_2.4H_2O$.

As noted above, the compounds of this invention can be converted, by hydrolysis, to a known herbicide, N-phosphonomethyliminodiacetic acid. To illustrate such a conversion, 5.0 grams of N-(diphenylphosphonomethyl) iminodiacetonitrile in 70 ml. of concentrated hydrochloric acid was boiled gently for about 22 hours. The mixture initially turned yellow during heating, then darkened and thereafter slowly lightened to yellow again. It was rotoevaporated to dryness and redissolved in 40 ml. of water. On cooling, 2.25 grams of crystalline solid precipitated, and nmr analysis showed this product to be N-phosphonomethyliminodiacetic acid. A 30.5 grams portion of the 72.8 grams of supernatant yellow filtrate was fractionated by high pressure liquid chromatography, and fractions 16–22 gave a further 0.34 grams of said product, which turned brown-orange at 215° C. and became a light foam at 218° C. No indication of N-phosphonomethylglycine was found in the product.

The post-emergent herbicidal activity of various compounds of this invention is demonstrated as follows. The active ingredients are applied in spray form to 14–21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Table I.

The post-emergent herbicidal activity index used in Table I is as follows:

| Plant Response | Index |
| --- | --- |
| 0–24% Inhibition | 0 |
| 25–49% Inhibition | 1 |
| 50–74% Inhibition | 2 |
| 75–99% Inhibition | 3 |
| All Killed | 4 |
| Species Not Present | * |

In said Table, the compounds are designated by the Example numbers, WAT indicates weeks after treatment, and the plant species treated are each represented by a code letter as follows:

A—Canada Thistle
B—Cocklebur
C—Velvetleaf
D—Morningglory
E—Lambsquarters
F—Smartweed
G—Yellow Nutsedge
H—Quackgrass
I'Johnsongrass
J—Downy Brome
K—Barnyardgrass

TABLE I

| Compound | WAT | kg h | A | B | C | D | E | F | G | H | I | J | K |
| --- | --- | --- | --- | --- | --- | --- | --- | --- | --- | --- | --- | --- | --- |
| 1 | 2 | 56.0 | 0 | 1 | 0 | 1 | 1 | 0 | 0 | 0 | 1 | 0 | 0 |
|  | 4 | 56.0 | 0 | 0 | 0 | 2 | 1 | 1 | 0 | 0 | 1 | 0 | 1 |
| 2 | 2 | 11.2 | 0 | 0 | 0 | 0 | 0 | 0 | 0 | 0 | 1 | 0 | 0 |
| 3 | 2 | 11.2 | 1 | * | 0 | 1 | 0 | 0 | 0 | 0 | 0 | 0 | 0 |
|  | 4 | 11.2 | 2 | * | 0 | 1 | 1 | 0 | 1 | 1 | 3 | 0 | 1 |
| 4 | 2 | 11.2 | 0 | * | 0 | 1 | 1 | 0 | 0 | 0 | 1 | 0 | 1 |
|  | 4 | 11.2 | 1 | * | 1 | 2 | 2 | 0 | 1 | 0 | 3 | 0 | 2 |
| 6 | 2 | 11.2 | 1 | 2 | 3 | 2 | 4 | 4 | 1 | 3 | 3 | 3 | 3 |
|  | 4 | 11.2 | 1 | 2 | 4 | 2 | 4 | 4 | 2 | 3 | 3 | 3 | 3 |
| 8 | 2 | 11.2 | 1 | 2 | 1 | 2 | 2 | 3 | 1 | 0 | 1 | 0 | 2 |
|  | 4 | 11.2 | 2 | 2 | 1 | 2 | 3 | 3 | 2 | 1 | 3 | 1 | 2 |

The pre-emergent herbicidal activity of various compounds of this invention is demonstrated as follows. A good grade of top soil is placed in aluminum pans and compacted to a depth of three-eighth to one-half inch from the top of each pan. A predetermined number of seeds or vegetative propagules of each of several plant species are placed on top of the soil in each pan and then pressed down.

In this method, the soil required to cover the seeds and propagules is weighed and admixed with a herbicidal composition, prepared as described in the post-emergence test, containing a known amount of active ingredient. The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period the number of emerged plants of each species is noted and compared to an untreated control. The data is given in Table II.

The pre-emergent herbicidal activity index used below is passed upon the average percent inhibition of each species as follows:

| Plant Response | Index |
| --- | --- |
| 0–25% Inhibition | 0 |
| 26–50% Inhibition | 1 |
| 51–75% Inhibition | 2 |
| 76–100% Inhibition | 3 |
| Species Not Present | * |

Plant species are identified in Table II by the same code letters used in Table I.

TABLE II

| Compound | kg h | A | B | C | D | E | F | G | H | I | J | K |
| --- | --- | --- | --- | --- | --- | --- | --- | --- | --- | --- | --- | --- |
| 1 | 11.2 | 0 | * | 0 | * | 0 | 0 | 0 | 0 | 1 | 0 | 0 |
| 3 | 11.2 | 1 | 0 | 0 | 0 | 2 | 0 | 0 | 0 | * | 0 | 0 |
| 4 | 11.2 | 3 | 0 | 0 | 0 | 1 | 0 | 0 | 0 | 0 | 0 | 0 |
| 5 | 11.2 | 0 | 1 | 0 | 1 | 0 | 2 | 0 | 0 | 0 | 0 | 3 |
| 6 | 11.2 | 2 | 0 | 0 | * | 0 | 0 | 0 | 0 | 0 | 0 | 0 |
| 8 | 11.2 | 0 | 0 | 0 | 0 | 0 | 0 | 0 | 0 | 3 | 0 | 0 |

It should be understood that each of the compounds in Examples 1–8 was tested for both post-emergent and pre-emergent activity. The absence of specific data for any individual compound in either of the Tables indicates that such compound showed a 0 index rating for all species in the test.

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acyl)taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powders of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicant and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention effective amounts of the active ingredient are applied to above-ground portions of plants or to the plant growth medium. The application of liquid and particulate solid herbicidal compositions can be carried out by conventional methods, e.g., soil incorporation, power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where inhibition of the aquatic plants is desired.

The application of an effective amount of the compounds of this invention to the plant is essential and critical for the practice of the present invention. The exact amount of active ingredient to be employed is dependent upon such factors as the plant species and stage of development thereof, and the amount of rainfall as well as the specific compound employed. In foliar or growth medium treatment for the inhibition of vegetative growth, the active ingredients are applied in amounts from about 0.56 to about 22.4 or more kilograms per hectare. In applications for the inhibition of aquatic plants, the active ingredients are applied in amounts of from about 0.1 parts per million to about 1000 parts per million, based on the aquatic medium. An effective amount for phytotoxic or herbicidal action is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

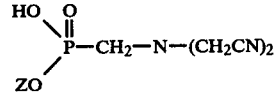

wherein Z is hydrogen or a herbicidally acceptable cation.

2. A compound as defined in claim 1 wherein Z is hydrogen.

3. A compound as defined in claim 1 wherein Z is a herbicidally acceptable cation.

4. A herbicidal composition comprising an inert adjuvant and a herbicidally effective amount of a compound of claim 1.

5. A herbicidal composition comprising an inert adjuvant and a herbicidally effective amount of a compound of claim 2.

6. A herbicidal composition comprising an inert adjuvant and a herbicidally effective amount of a compound of claim 3.

7. A herbicidal method which comprises applying to plants or the plant growth medium a herbicidally effective amount of a compound of claim 1.

8. A herbicidal method which comprises applying to plants or the plant growth medium a herbicidally effective amount of a compound of claim 2.

9. A herbicidal method which comprises applying to plants or the plant growth medium a herbicidally effective amount of a compound of claim 3.

* * * * *